United States Patent
Dosta et al.

(10) Patent No.: US 10,342,643 B2
(45) Date of Patent: Jul. 9, 2019

(54) DENTAL IMPLANT

(71) Applicant: Joint Stock Company "ALTIMED", Minsk (BY)

(72) Inventors: Anatoli D. Dosta, Minsk (BY); Aliaksandr I. Halauko, Minsk (BY)

(73) Assignee: Joint Stock Company "ALTIMED", Minsk (BY)

( * ) Notice: Subject to any disclaimer, the term of this patent is extended or adjusted under 35 U.S.C. 154(b) by 106 days.

(21) Appl. No.: 14/594,878

(22) Filed: Jan. 12, 2015

(65) Prior Publication Data

US 2015/0190214 A1    Jul. 9, 2015

Related U.S. Application Data

(63) Continuation of application No. PCT/BY2013/000003, filed on May 6, 2013.

(30) Foreign Application Priority Data

Jul. 12, 2012  (EA) .................................. 201201259

(51) Int. Cl.
    *A61C 8/00*    (2006.01)
(52) U.S. Cl.
    CPC .......... *A61C 8/0022* (2013.01); *A61C 8/0012* (2013.01); *A61C 8/0018* (2013.01); *A61C 2008/0046* (2013.01)
(58) Field of Classification Search
    CPC ...... A61C 8/0012–0098; A61B 5/6878; A61B 17/04; A61B 17/0401; A61B 2017/0403–0464
    (Continued)

(56) References Cited

U.S. PATENT DOCUMENTS 4,321,914 A * 3/1982 Begovac .......... A61M 39/0247
                                           128/887
4,359,318 A * 11/1982 Gittleman ............ A61C 8/0007
                                           433/173
(Continued)

FOREIGN PATENT DOCUMENTS

BY        11482 C1     12/2008
DE     19816865 A1     10/1999
(Continued)

OTHER PUBLICATIONS

International Search Report from International Application No. PCT/BY2013/000003, filed May 6, 2013, dated Sep. 26, 2013.
(Continued)

*Primary Examiner* — Nicholas D Lucchesi
(74) *Attorney, Agent, or Firm* — Patentbar International, P.C.

(57) ABSTRACT

A group of dental implants for the two-step implantation in the alveolar process is presented aiming to protect reliably the implantation area from ingress of the infection from the oral cavity due to the tight connection of the precervical side of the implant with the periodontal tissue. The set aim is achieved in the dental implant with the support to fix the dental prosthesis and the screw part for installation in the bone tissue, as well as with the ring head located between the dental prosthesis support and the screw part, made from the porous three-dimensional structure of the polymeric material and intended for ingrowth of the gum tissues, by means of the fact that the mentioned ring head is equipped with the reinforcing element made as a hollow body of revolution with apertures and located over the ring head.

7 Claims, 2 Drawing Sheets

(58) Field of Classification Search
USPC .................. 433/172–176; 623/16.11–23.63; 606/232, 233
See application file for complete search history.

(56) References Cited

U.S. PATENT DOCUMENTS

| | | | |
|---|---|---|---|
| 4,531,916 A | 7/1985 | Scantlebury et al. | |
| 4,988,351 A * | 1/1991 | Paulos | A61B 17/8625 606/232 |
| 5,167,502 A * | 12/1992 | Kawahara | A61C 8/0012 433/172 |
| 5,380,328 A * | 1/1995 | Morgan | A61B 17/8071 606/70 |
| 5,397,359 A * | 3/1995 | Mittelmeier | A61C 8/0012 623/1.5 |
| 5,433,607 A * | 7/1995 | Schmid | A61C 8/0031 433/173 |
| 5,944,526 A * | 8/1999 | Liu | A61C 8/0031 433/176 |
| 6,007,567 A * | 12/1999 | Bonutti | A61B 17/0401 606/232 |
| 6,095,817 A * | 8/2000 | Wagner | A61C 8/0012 433/173 |
| 6,257,890 B1 * | 7/2001 | Khoury | A61C 8/008 433/173 |
| 6,413,089 B1 * | 7/2002 | Ashman | A61C 8/0006 433/173 |
| 8,602,782 B2 * | 12/2013 | Lomicka | A61C 8/0012 433/174 |
| 8,899,982 B2 * | 12/2014 | Damstra | A61C 8/0012 433/174 |
| 9,095,396 B2 * | 8/2015 | Collins | A61C 8/0012 |
| 2004/0053196 A1 * | 3/2004 | Mayer | A61B 17/68 433/173 |
| 2007/0142861 A1 * | 6/2007 | Burkhart | A61B 17/0401 606/232 |
| 2009/0011384 A1 * | 1/2009 | Collins | A61C 8/0012 433/174 |
| 2009/0036908 A1 * | 2/2009 | Zokol | A61B 17/60 606/151 |
| 2009/0061388 A1 * | 3/2009 | Collins | A61C 8/0006 433/174 |
| 2009/0208907 A1 * | 8/2009 | Dosta | A61C 8/0009 433/174 |
| 2009/0291415 A1 * | 11/2009 | Binderman | A61C 8/0012 433/200.1 |
| 2009/0317768 A1 * | 12/2009 | Mayer | A61B 17/68 433/201.1 |
| 2010/0003640 A1 * | 1/2010 | Damstra | A61C 8/0012 433/201.1 |
| 2010/0114314 A1 * | 5/2010 | Lomicka | A61C 8/0033 623/16.11 |
| 2010/0198258 A1 * | 8/2010 | Heaven | A61B 17/0401 606/232 |
| 2010/0266987 A1 * | 10/2010 | Ford | A61C 8/0075 433/174 |
| 2011/0033825 A1 * | 2/2011 | Lee | A61B 17/8625 433/173 |
| 2011/0123951 A1 * | 5/2011 | Lomicka | A61C 8/0012 433/174 |
| 2011/0257753 A1 * | 10/2011 | Gordon | A61F 2/28 623/18.11 |
| 2012/0245632 A1 * | 9/2012 | Tsai | A61B 17/0401 606/232 |
| 2013/0344459 A1 * | 12/2013 | Collins | A61C 8/0012 433/174 |
| 2014/0017633 A1 * | 1/2014 | Lomicka | A61C 8/0012 433/174 |
| 2015/0056573 A1 * | 2/2015 | Collins | A61C 8/0012 433/174 |
| 2015/0320521 A1 * | 11/2015 | Battula | A61C 8/0006 433/173 |

FOREIGN PATENT DOCUMENTS

| | | |
|---|---|---|
| JP | H05-064646 A | 3/1993 |
| JP | 2006505339 A | 2/2006 |
| JP | 2010508094 A | 3/2010 |
| JP | 2010279653 A | 12/2010 |
| JP | 2013512006 A | 4/2013 |
| JP | 2014521434 A | 8/2014 |
| WO | 2005/105164 A1 | 11/2005 |
| WO | 2005/107829 A2 | 11/2005 |
| WO | 2010/139041 A1 | 12/2010 |

OTHER PUBLICATIONS

Gold, Martin, Medicare Lessons Learned from Spinal Fusion, Orthopedic. Design and Technology, Jan./Feb. 2007, pp. 16, 17.

* cited by examiner

DENTAL IMPLANT

RELATED APPLICATIONS

This Application is a Continuation Application of International Application PCT/BY2013/000003, filed on May 6, 2013, which in turn claims priority to Eurasian Patent Applications No. EA201201259, filed Jul. 12, 2012, both of which are incorporated herein by reference in their entirety.

FIELD OF THE INVENTION

The invention refers to dentistry, in particular, to the group of dental implants intended for the two-step implantation in the alveolar ridge.

BACKGROUND OF THE INVENTION

Destruction of the jaw bone in the precervical side of the implant is the clinical problem associated with dental implants. Such bone destruction is caused by the infectious etiology similar to that occurring in the case of diseases of periodontal tissues of natural teeth. Relationship between pathogenic organisms of periodontal tissues and destruction of the bone necessitates the careful oral hygiene, as well as possibility of timely prevention of the disease by a doctor and cure of the implantation place in the case of inflammation. Therefore, the dental implants with the smooth-surfaced precervical side are, as a rule, widely used in the clinical practice. The smooth surface of the precervical side of the dental implant is easy to be cleaned from the deposit, pathogenic germs and endotoxins, it promotes the accurate connection between the implant and the dental prosthesis support, thus preventing from appearance of a clearance between the mentioned components in future, what could be a "refuge" for pathogenic germs. However, though in contact with the bone, the smooth surface of the precervical side of the implant does not connect to the bone. As the surface contacting with the bone is accessible for the bacteria migrating from the oral cavity, the infection is transferred to the bone tissue, thus resulting in destruction of the bone where the implant has been installed into.

There is the implant [DE 19816865 A 1, 1999] containing the bioactive silicate glass coating in the zone of contact with the gum. The epithelial cells of the gum can interlock with the coating on the implant ensuring its firm fit in the jaw. However, the implant construction promotes the tissue ingrowth only, without stimulation of this process and without prevention from possible ingress of infection in the implantation zone.

There is the dental cylinder-shaped implant [BY11482, 30.12.2008], being the nearest prior art reference of the implant claimed, with the support to fix the dental prosthesis and the screw part for installation in the bone tissue, as well as with the ring head located between the dental prosthesis support and the screw part, made from the porous three-dimensional structure of the polymeric material and intended for ingrowth of the gum tissues. Such construction ensures ingrowth of soft tissues into the porous three-dimensional polymeric structure of the ring head, however, because of lack of strength of the porous three-dimensional polymeric structure, it does not ensure the reliable fixation of the implant in the alveolar process.

SUMMARY OF THE INVENTION

The aim of the invention claimed is to protect reliably the implantation area from ingress of the infection from the oral cavity due to the tight connection of the precervical side of the implant with the periodontal tissue.

The set aim is achieved in the dental implant with the support to fix the dental prosthesis and the screw part for installation in the bone tissue, as well as with the ring head located between the dental prosthesis support and the screw part, made from the porous three-dimensional structure of the polymeric material and intended for ingrowth of the gum tissues, by means of the fact that the ring head is equipped with the reinforcing element made as a hollow body of revolution with apertures and located over the ring head.

The reinforcing element is preferably made from the biologically compatible metal and the size of apertures of the reinforcing element is not less than the minimal size of pores of the mentioned porous three-dimensional polymeric structure.

The reinforcing element is preferably made with the free sections made as an upper ring for fixture to the mentioned support and a lower ring for fixation to the mentioned screw part of the implant.

Biocompatibility of the materials being used, strength of installation of the implant in the alveolar ridge, strong contact of the soft tissues (of the gum) with the implant surface are the main requirements in the process of implantation of dental constructions, and that are achieved both through the constructive features (availability of threads, grooves, indents, complex shape) and the materials being applied (biocompatible titanium alloys, titanium powders) and combination of two techniques mentioned.

The technical solution claimed allows achievement of compliance with the above-mentioned requirements to dental implants.

DETAILED DESCRIPTION OF THE PREFERRED EMBODIMENTS

Figure 1:
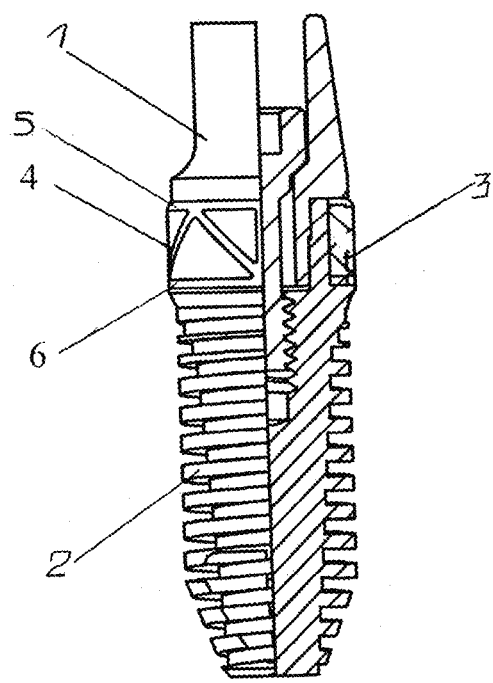
FIG. 1 is a general view of a dental implant of the present invention with a partial section.
Figure 2:
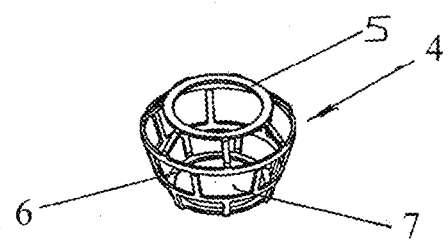
FIG. 2 is an illustration of an embodiment of a reinforcing element.

One of the forms of implementation of the dental implant claimed is represented on FIG. 1. The dental implant is made from a biocompatible material, such as titanium, and is shaped as a cylindrical body with the support 1 for fixation of the dental prosthesis and the screw part 2 for installation in the bone tissue, with the ring head 3 located between the support 1 of the dental prosthesis and the screw part 2, made from the porous three-dimensional structure of the polymeric material and intended for ingrowth of the gum tissues.

The ring 3 may be made both from polytetrafluoroethylene or polyesterketone (see [Orthopaedic. Design and Technology. January/February 2007]) and has the porous three-dimensional structure similar to known polymeric porous three-dimensional structures (see [WO 2005/107829]).

The reinforcing element 4 is made as a hollow body of revolution with apertures and located over the ring head 3. The free sections of the reinforcing element are made as an upper ring 5 fixed to the support 1, and a lower ring 6 fixed to the screw part 2.

The reinforcing element is made from the biologically compatible metal, e.g. is made from titanium wire by known technique of laser welding or is stamped from titanium foil.

The size of apertures 7 of the reinforcing element 4 is not less than the minimal size of pores of the mentioned porous three-dimensional polymeric structure of the ring head 3.

The implant is used as follows.

Example. The screw part 2 of the implant is to be screwed in the formed bone aperture 5 till coincidence of the alveolar ridge level with the ring head 3. The soft tissue of the gum is to be stitched to the butt of the ring 3, the stitches are to be fastened to the reinforcing element 4.

Availability of the head ring 3 stimulates ingrowth of the soft tissues and prevents the implantation area from ingress of infection. After final engraftment the tooth body is to be formed on the support 1 (not shown on drawings).

Figure 3A:
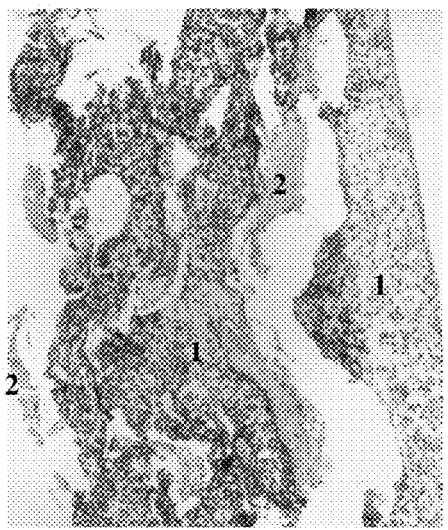
FIGS. 3A-3D are microphotographs of histological specimens.
Figure 3B:
Figure 3C:
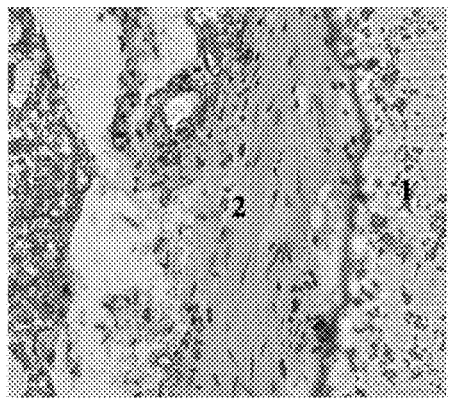

The results of interaction of the gum tissues with the porous structure claimed are illustrated with the microphotos of histological specimens represented on FIG. 3A-3C, where the digits mean the following: 1—polytetrafluoroethylene (it does not absorb stains); 2—fibrous connective tissue; 3—multi-layer non-keratinizing epithelium. The microphotos are made with magnification: A—x50; B—100; C, D—x400.

Figure 3D:
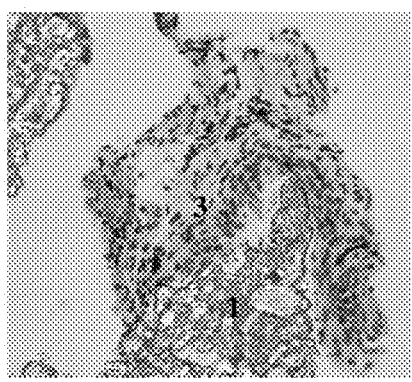

In the course of the histological study it was found that the dense fibrous connective tissue interacts with the ring head around the dental cervix. This tissue adjoins to the ring surface, as well as enters the pores of the material it is made from (FIG. 3A, 3B). One can clearly see bundles of collagen fibers, as well as large number of fibroblasts (FIG. 3C) on the histological specimens stained with hematoxylin and eosin, with large magnification. Presence of fragments of the multi-layer non-keratinizing epithelium interacting with the polytetrafluoroethylene insert of the dental implant (FIG. 3D) was found in the specimens studied.

Thus, the technical result of the invention claimed is creation of the conditions for successful ingrowth of the soft tissues in the implant due to reduction of complications in the operative and post-operative periods, and this ensure the reliable fixation of the implant.

What is claimed is:

1. A dental implant, comprising:
    a support for attaching to a dental prosthesis;
    a monolithic cylindrical screw part having a threaded section for screwing in bone tissue and affixed to the support by a set screw;
    a ring head made from a porous polymeric material and enveloping adjacent portions of: (i) the support and (ii) the screw part; and
    a perforated circular element disposed on an outer surface of the ring head, said circular element having (i) diagonal ribs for supporting stitches fastening gum tissue to the implant and (ii) sidewall apertures exposing regions of the ring head.

2. The dental implant of claim 1, wherein openings of the apertures are dimensionally not smaller than pores of the polymeric material.

3. The dental implant of claim 1, wherein the circular element comprises sections adapted for attaching the element to the support or screw part.

4. The dental implant of claim 1, wherein the circular element is made from a titanium wire or stamped titanium foil.

5. The dental implant of claim 1, wherein the ring head is made from polytetrafluoroethylene or polyesterketone.

6. A dental implant, comprising:
    a support for attaching to a dental prosthesis, the support made from a first biocompatible material;
    a monolithic cylindrical screw part made from a second biocompatible material, said screw part having a threaded section for screwing in bone tissue and affixed to the support by a set screw;
    a ring head made from polytetrafluoroethylene or polyesterketone and enveloping adjacent portions of: (i) the support and (ii) the screw part; and
    a perforated circular element made of a third biocompatible material and disposed on an outer surface of the ring head, said circular element having (i) diagonal ribs for supporting stitches fastening gum tissue to the implant and (ii) sidewall apertures exposing regions of the ring head.

7. The dental implant of claim 6, wherein:
    the first and second biocompatible material is titanium; and
    the third biocompatible material is a titanium wire or stamped titanium foil.

* * * * *